(12) United States Patent
Nobis et al.

(10) Patent No.: US 8,388,653 B2
(45) Date of Patent: Mar. 5, 2013

(54) T-TYPE SUTURE ANCHORING DEVICES AND METHODS OF USING SAME

(75) Inventors: Rudolph H. Nobis, Mason, OH (US); Frank Jankoski, Phillipsburg, NJ (US); Omar J. Vakharia, Mason, OH (US); John A. Faux, Cincinnati, OH (US); Gregory J. Bakos, Mason, OH (US); Duane A. Linenkugel, Cincinnati, OH (US); Christopher Paul Swain, London (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1401 days.

(21) Appl. No.: 11/127,513

(22) Filed: May 12, 2005

(65) Prior Publication Data

US 2006/0025819 A1  Feb. 2, 2006

Related U.S. Application Data

(60) Provisional application No. 60/571,117, filed on May 14, 2004, provisional application No. 60/571,119, filed on May 14, 2004, provisional application No. 60/571,000, filed on May 14, 2004.

(51) Int. Cl.
  *A61B 17/04* (2006.01)
(52) U.S. Cl. ...................................................... 606/232
(58) Field of Classification Search ................... 606/151, 606/169, 222, 228, 232, 113; 227/67, 68; 600/471, 104
See application file for complete search history.

(56) References Cited

U.S. PATENT DOCUMENTS

| | | | |
|---|---|---|---|
| 3,125,095 A * | 3/1964 | Kaufman et al. | 606/228 |
| 4,235,238 A | 11/1980 | Ogiu et al. | |
| 5,123,914 A | 6/1992 | Cope | |
| 5,269,809 A | 12/1993 | Hayhurst et al. | |
| 5,370,661 A | 12/1994 | Branch | |
| 5,409,499 A | 4/1995 | Yi | |
| 5,527,341 A | 6/1996 | Gogolewski et al. | |
| 5,562,689 A | 10/1996 | Green et al. | |
| 5,584,840 A | 12/1996 | Ramsey et al. | |
| 5,669,917 A | 9/1997 | Sauer et al. | |
| 5,810,853 A | 9/1998 | Yoon | |
| 5,899,921 A | 5/1999 | Caspari et al. | |
| 5,902,231 A | 5/1999 | Caspari et al. | |
| 5,902,321 A | 5/1999 | Caspari et al. | |
| 5,911,728 A | 6/1999 | Sepetka et al. | |
| 5,984,933 A | 11/1999 | Yoon | |
| 6,045,571 A * | 4/2000 | Hill et al. | 606/228 |
| 6,068,648 A | 5/2000 | Cole et al. | |

(Continued)

FOREIGN PATENT DOCUMENTS

| | | |
|---|---|---|
| WO | WO 9308747 A1 | 5/1993 |
| WO | WO 96/22735 A | 8/1996 |
| WO | WO 01/66001 A | 9/2001 |

OTHER PUBLICATIONS

Co-pending U.S. Appl. No. 60/571,117, filed May 14, 2004, Jesse J. Kuhns.

(Continued)

*Primary Examiner* — Julian Woo

(57) ABSTRACT

Suture anchoring devices are disclosed, including a T-tag anchoring device that is suitably small enough to fit into the hollow tip of a needle and, furthermore, provide protection to the suture against being cut or otherwise damaged by the sharp edge of the needle tip. One disclosed device includes a slot for providing a pivot point between the suture and the body when deployed, which can be employed to form a T-tag.

16 Claims, 7 Drawing Sheets

U.S. PATENT DOCUMENTS

| | | |
|---|---|---|
| 6,200,329 B1 | 3/2001 | Fung et al. |
| 6,306,156 B1 | 10/2001 | Clark |
| 6,352,503 B1 * | 3/2002 | Matsui et al. ................. 600/104 |
| 6,387,104 B1 | 5/2002 | Pugsley, Jr. et al. |
| 6,596,014 B2 * | 7/2003 | Levinson et al. ............. 606/228 |
| 6,648,903 B1 | 11/2003 | Pierson, III |
| 6,652,561 B1 * | 11/2003 | Tran ............................. 606/232 |
| 6,773,436 B2 | 8/2004 | Donnelly et al. |
| 6,776,784 B2 * | 8/2004 | Ginn ............................. 606/151 |
| 2003/0158581 A1 | 8/2003 | Levinson |
| 2003/0191497 A1 | 10/2003 | Cope |

OTHER PUBLICATIONS

Co-pending U.S. Appl. No. 60/571,119, filed May 14, 2004, Rudolph H. Nobis.

Co-pending U.S. Appl. No. 60/571,000, filed May 14, 2004, Rudolph H. Nobis.

Co-pending U.S. Appl. No. 11/127,515, filed May 12, 2005, Jesse J. Kuhns.

Co-pending U.S. Appl. No. 11/127,955, filed May 12, 2005, Rudolph H. Nobis.

* cited by examiner

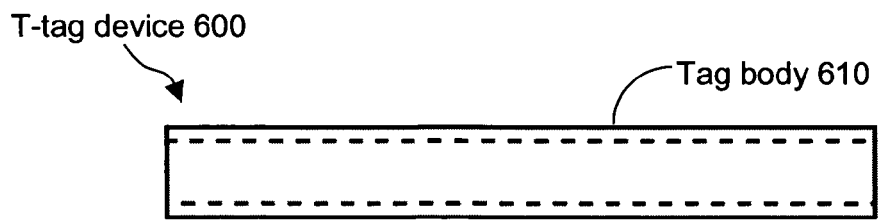
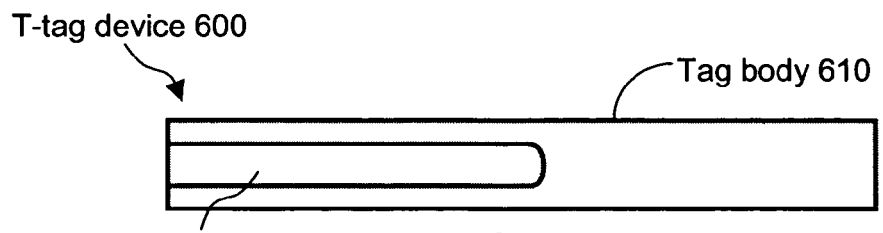
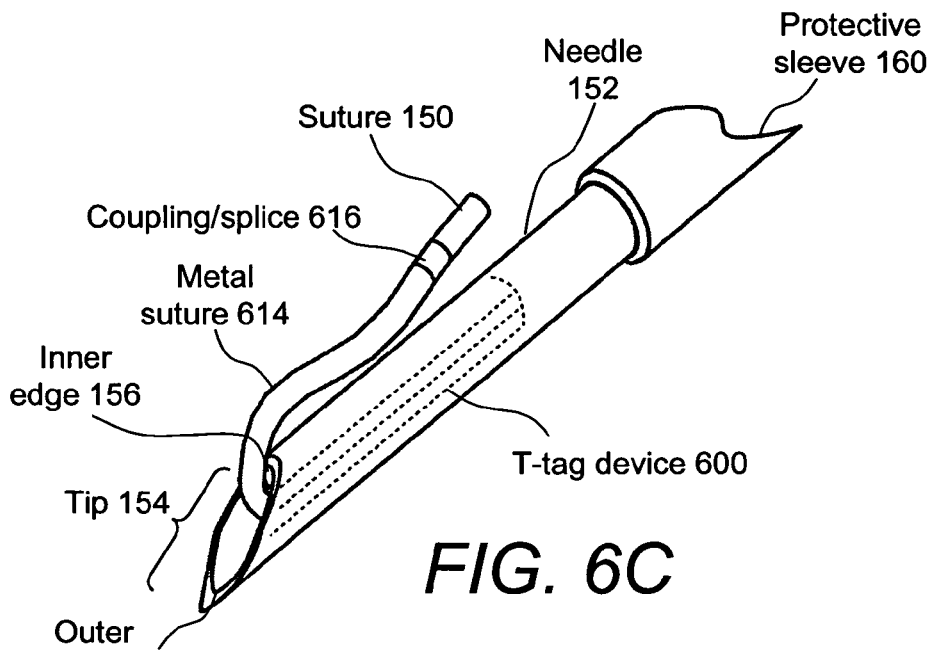
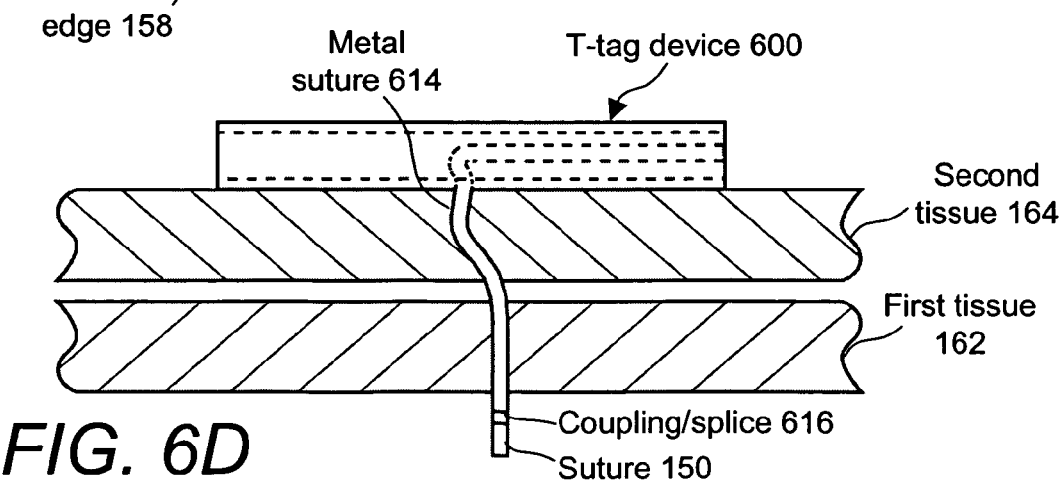

T-TYPE SUTURE ANCHORING DEVICES AND METHODS OF USING SAME

CROSS-REFERENCES TO RELATED APPLICATIONS

This application claims priority to and incorporates by reference the following applications: U.S. Provisional Application 60/571,117 filed May 14, 2004; U.S. provisional Application 60/571,119 filed May 14, 2004; and U.S. Provisional Application 60/571,000 filed May 14, 2004.

FIELD OF THE INVENTION

This invention relates to an endoscopic suturing device. More particularly, this invention relates to devices that can be sized to fit into the tip of a standard endoscopic ultrasound (EUS) needle.

BACKGROUND

Application of sutures in the gastrointestinal tract is required for several different types of medical procedures, for example, for transoral endoscopic valvuloplasty for gastroesophageal reflux disease (GERD), gastroplasty, fundoplication, anterior gastropexy, posterior gastropexy, suturing esophageal perforations, or closure of the esophageal side of the tracheo-esophageal fistula. Traditionally, these procedures are performed by physicians, such as gastroenterologists or surgeons, either by laparoscopy or open surgical techniques. Such procedures are invasive, as laparoscopy requires that small access incision(s) be made in the body of the patient, through which a laparoscope and other surgical enabling tools are provided, while open surgical techniques are traditionally invasive and can have complications and cause long patient recovery periods.

The solution to these problems is to perform these medical procedures through the gastroesophageal tract via the mouth or other naturally occurring orifice. Already available flexible endoscopes, commonly called gastroscopes, can be provided through the gastroesophageal tract and enable illumination and visualization of tissue along the gastroesophageal tract on a video display for diagnostic purposes. These flexible endoscopes also provide an instrumentation means for applying sutures in tissue, such as in the wall of the stomach. What is needed are improved methods of providing a totally transoral surgical procedure, such as a posterior gastropexy procedure, and thereby avoid more-invasive laparoscopic procedures.

New endoscopic suturing methods performed through the gastroesophageal tract as an alternative to the invasive laparoscopic method of, for example, a posterior gastropexy procedure, are currently being developed. For example, suturing methods under the control of endoscopic ultrasound (EUS) are being evaluated. EUS is a procedure that combines endoscopy and ultrasound. In particular, a Mar. 14, 2003 publication authored by Fritscher-Ravens, Mosse, Mukherjee, Yazaki, Park, Mills, and Swain, entitled, "Transgastric gastropexy and hiatal hernia repair for GERD under EUS control: a porcine model," (American Society for Gastrointestinal Endoscopy) describes how endoluminal operations for gastroesophageal reflux are currently limited by the inability of the surgeon to visualize and manipulate structures outside the wall of the gut. The publication describes a way to define the EUS anatomy of structures outside the gut that influence reflux, to place stitches in the median arcuate ligament (MAL), to perform posterior gastropexy, and to test the feasibility of crural repair, under EUS control, in pigs. More specifically, by using a linear-array EUS, the MAL and part of the right crus were identified and punctured with a needle, which served as a carrier for a tag and suture. These were anchored into the muscle. An endoscopic sewing device was used, which allowed stitches to be placed through a 2.8-mm accessory channel to any predetermined depth.

The publication also describes new methods of knot tying and suture cutting through the 2.8-mm channel of the EUS. More specifically, stitches were placed through the gastric wall into the MAL, and one stitch was placed just beyond the wall of the lower esophageal sphincter. The stitches were tied together and locked against the gastric wall, and the surplus length of suture material was then cut and removed. While this publication describes a suitable transgastric gastropexy and hiatal hernia repair procedure, further improvements in methodology and equipment to perform such procedures would be beneficial. For example, the publication describes a process for placing stitches in the MAL, which involves placing a suture anchor device, e.g., a T-tag, into the MAL by using an EUS needle. However, the EUS needle, which serves as the carrier for the tag and suture, requires modification, in order to prevent the suture from being cut on the needle's sharp edge. More specifically, the EUS needle was modified by the addition of a slot in which the suture lies and by which clearance is provided to prevent the suture from being cut on the needle's sharp edge. This needle modification process adds complexity and cost to the medical procedure. What is needed are suture tag devices that may be deployed by the use of an unmodified, commercially available EUS needle. Additionally, what is needed is way to deploy a suture tag device by the use of an unmodified commercially available EUS needle while protecting the suture from being cut by the needle's sharp edge.

SUMMARY OF THE INVENTION

Applicants recognize that it would be beneficial to provide suturing devices, such as suture tag devices, that are suitably small enough to fit into and be deployed by an unmodified, commercially available EUS needle.

Applicants recognize that it would be beneficial to provide suture devices, such as suture tag devices, that provide protection against the suture's being cut or otherwise damaged by the sharp edges when it inserted into a commercially available EUS needle.

Certain embodiments of the present invention are directed to providing improved devices for anchoring sutures into body tissue when medical procedures, such as a posterior gastropexy procedure, are performed, and thereby allowing commercially available hypodermic needles to be used without modification as carriers for a tag and suture. Certain embodiments of the present invention provide a T-tag anchoring device that is suitably small enough to fit into the hollow tip of a standard needle and, furthermore, provide protection against the suture's being cut by the sharp edges of the needle tip.

Certain embodiments of the invention provide a cylindrical hollow body that is suitably small enough to fit into a standard needle and into which a suture is attached. Furthermore, the body includes a slot for providing a pivot point between the suture and the body, when deployed, which thereby forms a T-tag. Certain embodiments provide features built into the body for protecting the suture from the sharp edges of the needle. Alternatively, certain other embodiments provide protective sleeves around the suture that, likewise, provide protection against cutting.

In another embodiment of the invention, rather than inserting the body inside the hollow needle, a cylindrical hollow body is provided that is sized to fit over the outside diameter of a standard needle that has the suture attached therein. Furthermore, the body includes a hole for providing a pivot point between the suture and the body when deployed, thereby forming a T-tag. In this embodiment, the suture is not in physical contact with the sharp edges of the needle and, thus, there is no danger that the suture will be cut.

BRIEF DESCRIPTION OF THE DRAWINGS

While the novel features of the invention are set forth with particularity in the appended claims, the invention, in all its embodiments, may be more fully understood with reference to the following description and accompanying drawings.

FIG. 6A illustrates a side view of a suture T-tag device in accordance with a sixth embodiment of the invention;

FIG. 6B illustrates a bottom view of the suture T-tag device of the sixth embodiment of the invention;

FIG. 6C illustrates a perspective view of the suture T-tag device of the sixth embodiment of the invention being deployed with a standard needle;

FIG. 6D illustrates a side view of the suture T-tag device of the sixth embodiment of the invention in use after being deployed.

DETAILED DESCRIPTION OF THE INVENTION

Figure 1A:
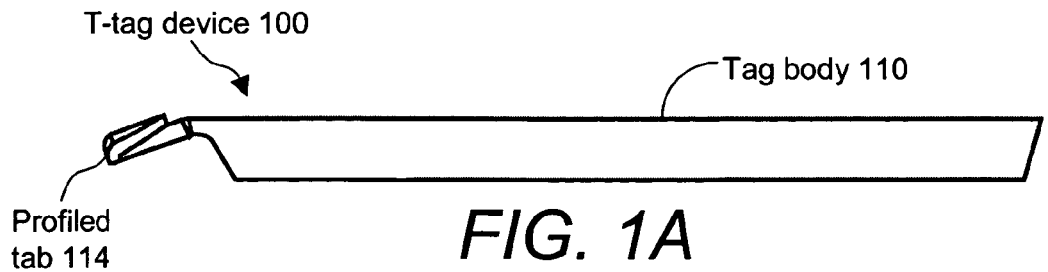
FIG. 1A illustrates a side view of a suture T-tag device in accordance with a first embodiment of the invention.
Figure 1B:
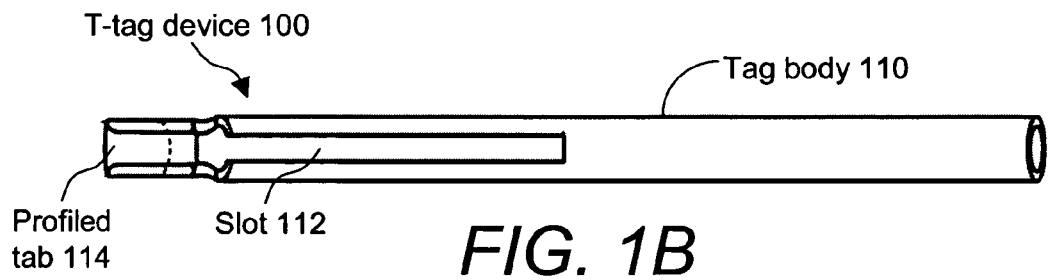
FIG. 1B illustrates a bottom view of the suture T-tag device of the first embodiment of the invention.

FIGS. 1A and 1B illustrate a side and bottom view, respectively, of a T-tag device 100 in accordance with a first embodiment of the invention. T-tag device 100 includes a cylindrical tag body 110. The outside diameter of tag body 110 is small enough to fit within the hollow tip of a standard EUS needle, which typically has an inside diameter of about 0.034 inches. The inside diameter of tag body 110 is sized to accommodate a length of suture material, which has an outside diameter that typically ranges from 0.004 to 0.010 inches. T-tag device 100 further includes a slot 112 within the wall of tag body 110. Slot 112 runs from one end of tag body 110 to approximately midway of tag body 110 and is suitably wide enough to accommodate a suture passing therethrough. Furthermore, arranged at the end of tag body 110, which has slot 112, is a profiled tab 114. T-tag device 100 is formed of, for example, molded plastic or stainless steel.

Figure 1C:
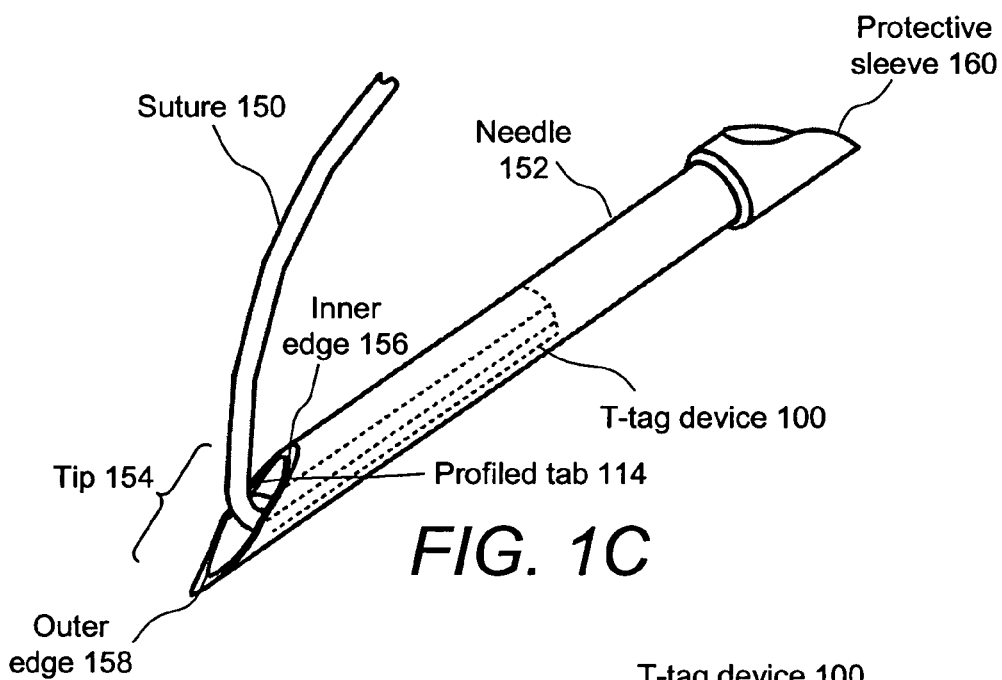
FIG. 1C illustrates a perspective view of the suture T-tag device of the first embodiment of the invention being deployed with a standard needle.

FIG. 1C illustrates a perspective view of T-tag device 100 of the first embodiment of the invention being deployed with a standard needle, such as an EUS needle manufactured by Wilson-Cook (Winston-Salem, N.C.). More specifically, FIG. 1C shows T-tag device 100 with a length of standard suture material, i.e., a suture 150, installed therein and inserted into the hollow tip of a standard needle 152. A sharp tip 154 of needle 152 is angled and, thus, its opening has an elliptical shape with sharp edges, i.e., an inner edge 156 and an outer edge 158. Additionally, a protective sleeve 160 surrounds the hollow shaft of needle 152. Needle 152 is axially slidable within protective sleeve 160.

The angle of profiled tab 114 matches the angle of tip 154, and the shape of profiled tab 114 matches the elliptical shape of inner edge 156 of tip 154. Critical to the operation of T-tag device 100, the overall outside dimension of profiled tab 114, in combination with tag body 110, cannot be less than the inside diameter of needle 152 and cannot be greater than the outside diameter of needle 152. Profiled tab 114 also orients T-tag device 100 and prevents it from rotating inside needle 152. See Table 1 for example dimensions of T-tag device 100.

TABLE 1

Example dimensions of T-tag device 100

| | Example Dimension |
|---|---|
| Tag body 110 length | 0.497 inches |
| Tag body 110 outside diameter | 0.030 inches |
| Tag body 110 inside diameter | 0.020 inches |
| Slot 112 length | 0.245 inches |
| Slot 112 width | 0.014 inches |
| Profiled tab 114 angle | 20 degrees |

Figure 1D:
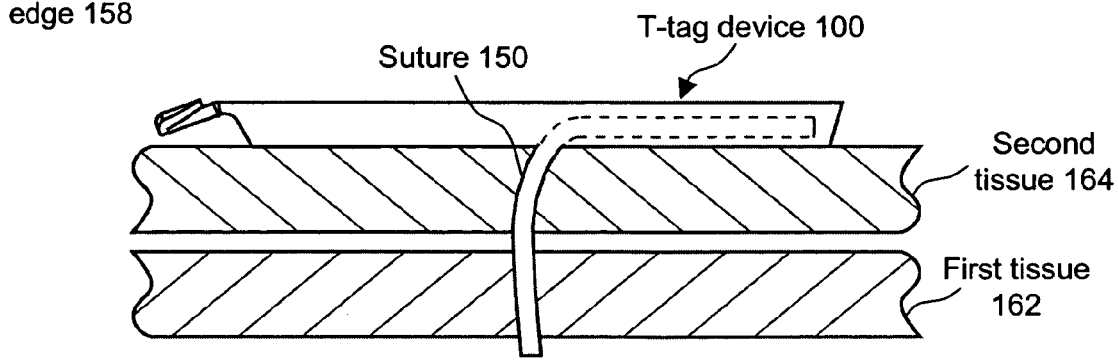
FIG. 1D illustrates a side view of the suture T-tag device of the first embodiment of the invention in use after being deployed.

The operation of T-tag device 100 is described in reference to FIGS. 1A, 1B, 1C, and FIG. 1D, which illustrates a side view of T-tag device 100 of the first embodiment of the invention in use after being deployed. An end of suture 150 is inserted through slot 112 and secured into the end of tag body 110 opposite slot 112. Methods of securing suture 150 within tag body 110 include swaging, crimping, knotting, or gluing. With suture 150 lying axially within slot 112, the end of tag body 110 opposite profiled tab 114 is inserted into hollow tip 154 of needle 152, until such point that profiled tab 114 abuts inner edge 156 of the opening of needle 152 and a length of suture 150 remains outside needle 152. With T-tag device 100 loaded within needle 152, the user pushes needle 152 through a first tissue 162 and then through a second tissue 164. After needle 152 passes through second tissue 164, the user pushes a stylet (not shown), i.e., a pushrod, that is part of the needle assembly against the proximal end of T-tag device 100, which forces T-tag device 100 to exit needle 152. The user then withdraws needle 152 from first tissue 162 and second tissue 164 and, subsequently, applies traction upon suture 150. The pulling action upon suture 150 causes tag body 110 to pivot upon suture 150 at the inner edge of slot 112, as suture 150 forms a 90-degree angle (or nearly so) with slot 112 and, thus, tag body 110 aligns itself against second tissue 164, as shown in FIG. 1D. The user then locks and cuts the opposite end of suture 150 (locking and cutting mechanisms not shown).

Figure 2A:
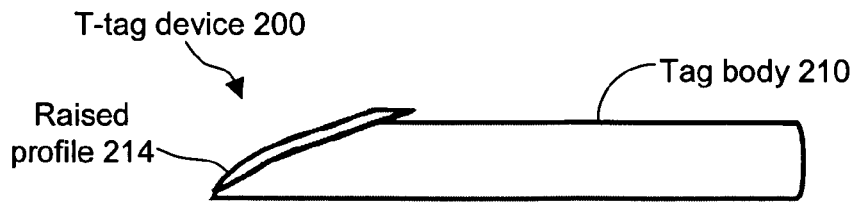
FIG. 2A illustrates a side view of a suture T-tag device in accordance with a second embodiment of the invention.
Figure 2B:
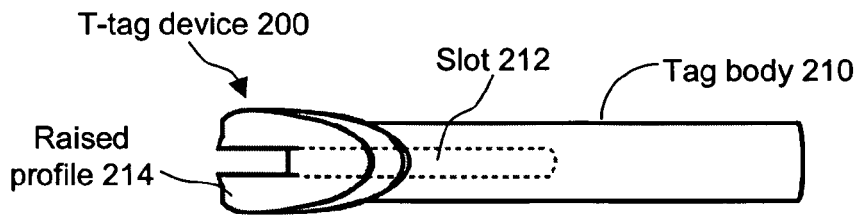
FIG. 2B illustrates a top view of the suture T-tag device of the second embodiment of the invention.

FIGS. 2A and 2B illustrate a side and top view, respectively, of a T-tag device 200 in accordance with a second embodiment of the invention. T-tag device 200 includes a cylindrical tag body 210. The outside diameter of tag body 210 is small enough to fit within the hollow tip of a standard EUS needle, which typically has an inside diameter of about 0.034 inches. The inside diameter of tag body 210 is sized to accommodate a length of suture material, which is typically about 0.009 inches in thickness. T-tag device 200 further includes a slot 212 within the wall of tag body 210. Slot 212 runs from one end of tag body 210 to approximately midway of tag body 210 and is suitably wide enough to accommodate suture 150 passing therethrough. Furthermore, arranged at the end of tag body 210, which has slot 212, is a raised profile 214. T-tag device 200 is formed of, for example, molded plastic or coined stainless steel.

Figure 2C:
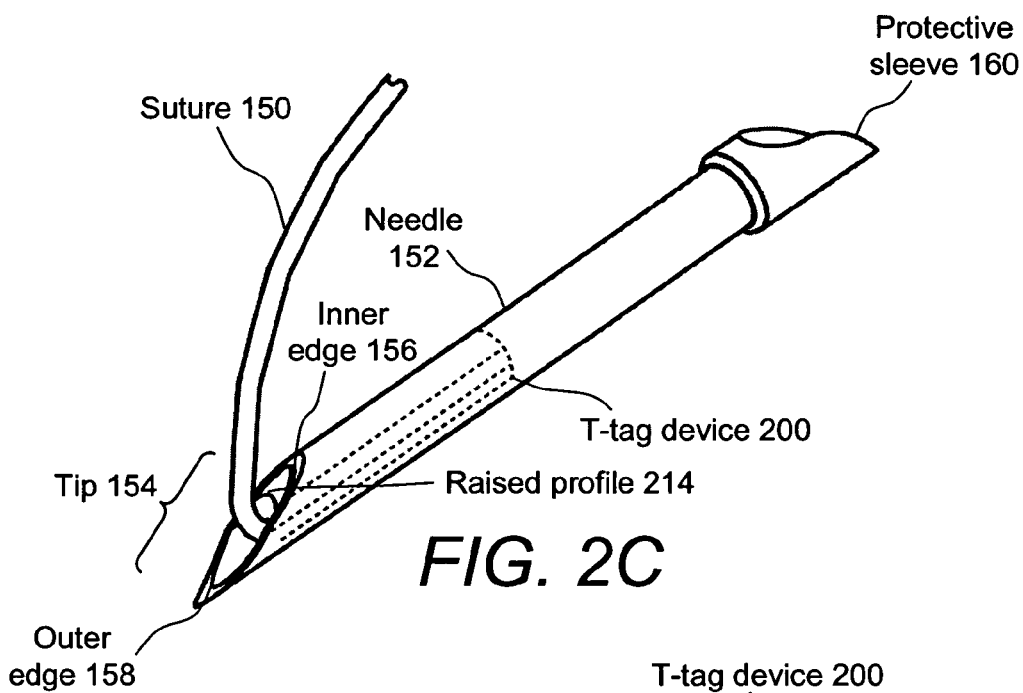
FIG. 2C illustrates a perspective view of the suture T-tag device of the second embodiment of the invention being deployed with a standard needle.

FIG. 2C illustrates a perspective view of T-tag device 200 of the second embodiment of the invention being deployed with a standard needle, such as a Wilson-Cook EUS needle. More specifically, FIG. 2C shows T-tag device 200 with suture 150 installed therein and inserted into the hollow tip of standard needle 152, which is slidable within protective sleeve 160. The sharp tip 154 of needle 152 is angled and, thus, its opening has an elliptical shape with sharp edges, i.e., inner edge 156 and outer edge 158, as described in reference to FIG. 1C.

The angle of raised profile 214 matches the angle of tip 154, and the shape of raised profile 214 matches the elliptical shape of inner edge 156 of tip 154. Critical to the operation of T-tag device 200, the overall outside dimension of raised profile 214, in combination with tag body 210, cannot be less than the inside diameter of needle 152 and cannot be greater than the outside diameter of needle 152. Raised profile 214 also orients T-tag device 200 and prevents it from rotating inside needle 152. See Table 2 for example dimensions of T-tag device 200.

TABLE 2

Example dimensions of T-tag device 200

| | Example Dimension |
|---|---|
| Tag body 210 length | 0.234 inches |
| Tag body 210 outside diameter | 0.032 inches |
| Tag body 210 inside diameter | 0.012 inches |
| Slot 212 length | 0.16 inches |
| Slot 212 width | 0.012 inches |

TABLE 2-continued

Example dimensions of T-tag device 200

| | Example Dimension |
|---|---|
| Height of raised profile 214 above the outer surface of tag body 210 | 0.005 inches |
| Raised profile 214 angle | 20.0 degrees |

Figure 2D:
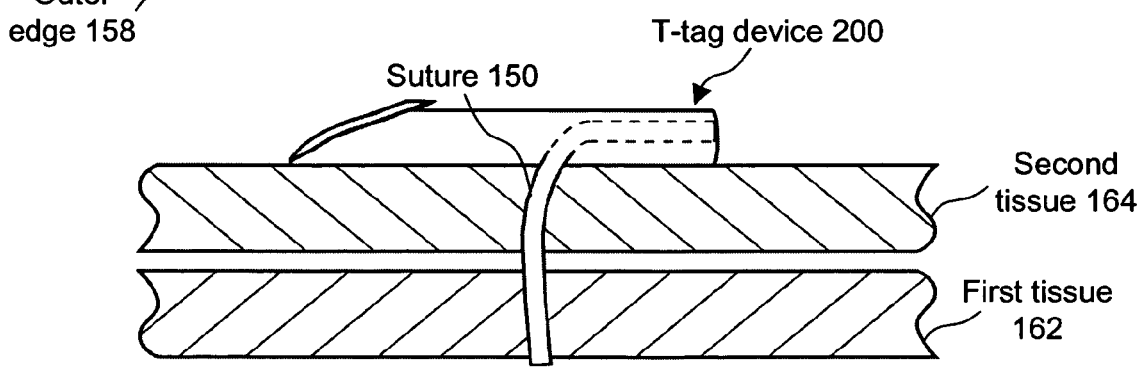
FIG. 2D illustrates a side view of the suture T-tag device of the second embodiment of the invention in use after being deployed.

The operation of T-tag device 200 is described in reference to FIGS. 2A, 2B, 2C, and FIG. 2D, which illustrates a side view of T-tag device 200 of the second embodiment of the invention in use after being deployed. An end of suture 150 is inserted through slot 212 and secured into the end of tag body 210 opposite slot 212. Methods of securing suture 150 within tag body 210 include swaging, crimping, knotting, or gluing. With suture 150 lying axially within slot 212, the end of tag body 210 opposite raised profile 214 is inserted into hollow tip 154 of needle 152, until such point that raised profile 214 abuts inner edge 156 of the opening of needle 152 and a length of suture 150 remains outside needle 152. With T-tag device 200 loaded within needle 152, the user pushes needle 152 through first tissue 162 and then through second tissue 164. After needle 152 passes through second tissue 164, the user pushes a stylet (not shown) against the proximal end of T-tag device 200, which forces T-tag device 200 to exit needle 152. The user then withdraws needle 152 from first tissue 162 and second tissue 164 and, subsequently, applies traction upon suture 150. The pulling action upon suture 150 causes tag body 210 to pivot upon suture 150 at the inner edge of slot 212, as suture 150 forms a 90-degree angle (or nearly so) with slot 212 and, thus, tag body 210 aligns itself against second tissue 164, as shown in FIG. 2D. The user then locks and cuts the opposite end of suture 150 (locking and cutting mechanisms not shown).

Figure 3A:
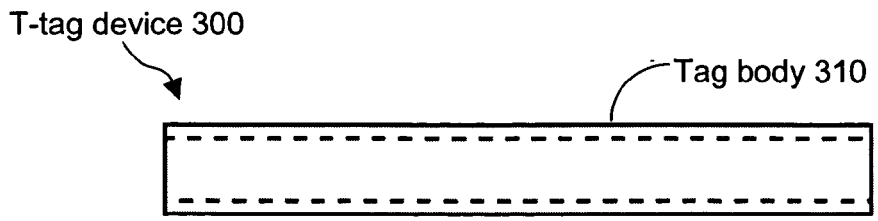
FIG. 3A illustrates a side view of a suture T-tag device in accordance with a third embodiment of the invention.
Figure 3B:
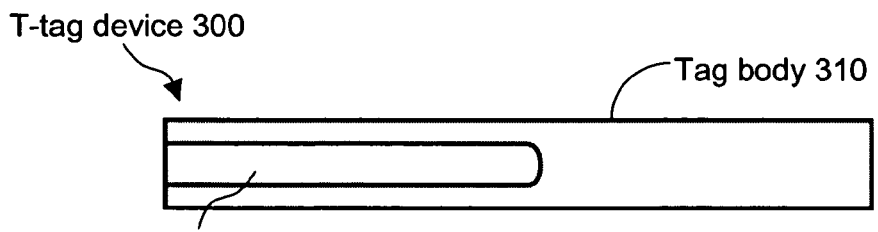
FIG. 3B illustrates a bottom view of the suture T-tag device of the third embodiment of the invention.

FIGS. 3A and 3B illustrate a side and bottom view, respectively, of a T-tag device 300 in accordance with a third embodiment of the invention. T-tag device 300 includes a cylindrical tag body 310. The outside diameter of tag body 310 is small enough to fit within the hollow tip of a standard EUS needle, which typically has an inside diameter of about 0.034 inches. The inside diameter of tag body 310 is sized to accommodate a flexible sleeve 314 (see FIG. 3C), which has suture 150 fitted therein. The outside diameter of flexible sleeve 314 typically ranges from 0.010 to 0.020 inches. T-tag device 300 further includes a slot 312 within the wall of tag body 310. Slot 312 runs from one end of tag body 310 to approximately midway of tag body 310 and is suitably wide enough to accommodate flexible sleeve 314 passing therethrough. T-tag device 300 is formed of, for example, molded plastic or coined stainless steel. Flexible sleeve 314 is formed of extruded or cast polymer material, such as Polyimide. Alternatively, flexible sleeve 314 is formed of flexible woven stainless steel.

Figure 3C:
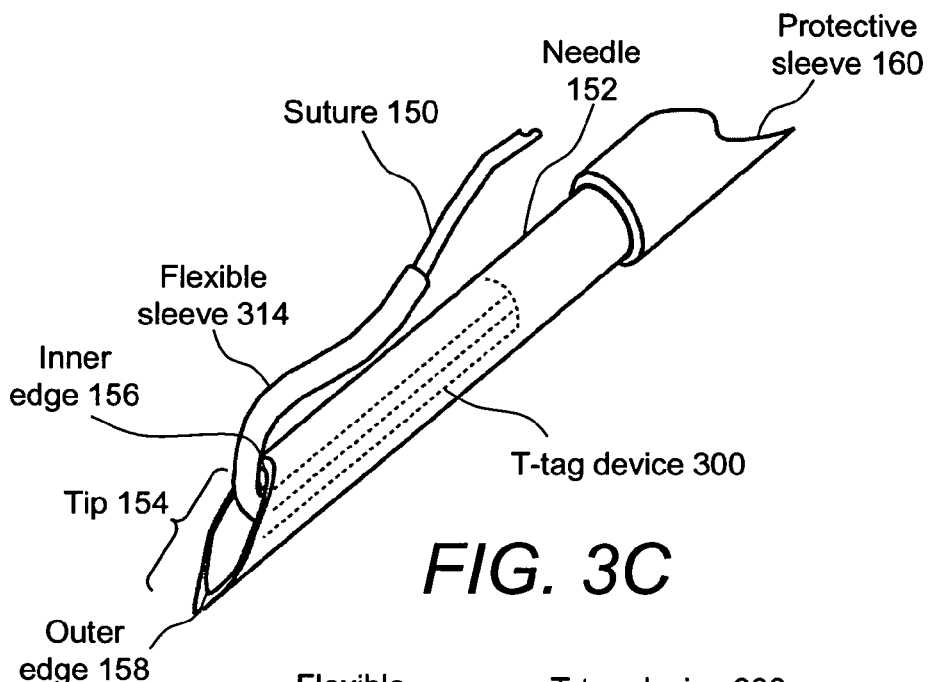
FIG. 3C illustrates a perspective view of the suture T-tag device of the third embodiment of the invention being deployed with a standard needle.

FIG. 3C illustrates a perspective view of T-tag device 300 of the third embodiment of the invention being deployed with a standard needle, such as a Wilson-Cook EUS needle. More specifically, FIG. 3C shows T-tag device 300 with flexible sleeve 314, within which suture 150 is fitted, installed therein and inserted into the hollow tip of standard needle 152 that is slidable within protective sleeve 160. The sharp tip 154 of needle 152 is angled and, thus, its opening has an elliptical shape with sharp edges, i.e., inner edge 156 and outer edge 158, as described in reference to FIG. 1C. Flexible sleeve 314 provides a protective barrier between suture 150 and the sharp inner edge 156 of needle 152. See Table 3 for example dimensions of T-tag device 300.

TABLE 3

Example dimensions of T-tag device 300

| | Example Dimension |
|---|---|
| Tag body 310 length | 0.25 inches |
| Tag body 310 outside diameter | 0.03 inches |
| Tag body 310 inside diameter | 0.02 inches |
| Slot 312 length | 0.125 inches |
| Slot 312 width | 0.02 inches |
| Flexible sleeve 314 length | 0.50 inches |
| Flexible sleeve 314 outside diameter | 0.015 inches |
| Flexible sleeve 314 inside diameter | 0.010 inches |

Figure 3D:
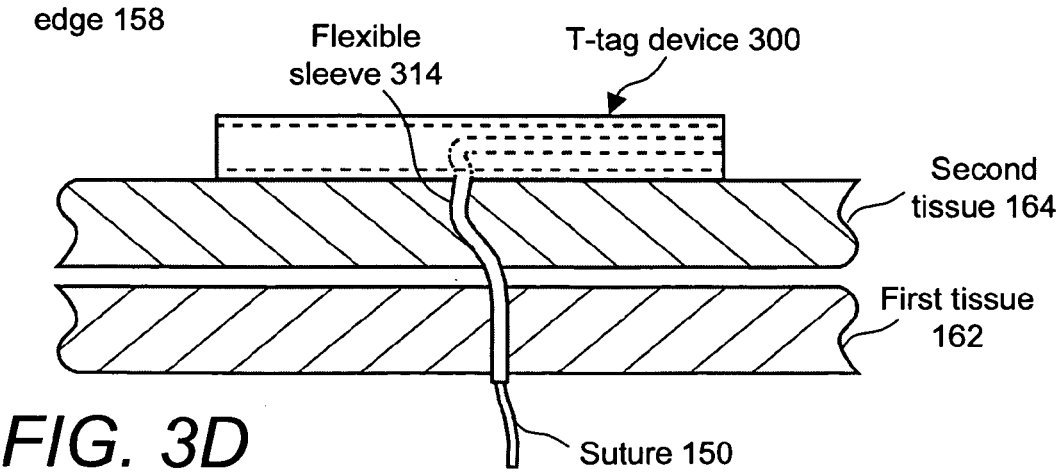
FIG. 3D illustrates a side view of the suture T-tag device of the third embodiment of the invention in use after being deployed.

The operation of T-tag device 300 is described in reference to FIGS. 3A, 3B, 3C, and FIG. 3D, which illustrates a side view of T-tag device 300 of the third embodiment of the invention in use after being deployed. An end of flexible sleeve 314 with suture 150 fitted therein is inserted through slot 312 and secured into the end of tag body 310 opposite slot 312. Methods of securing flexible sleeve 314 within tag body 310 include swaging, crimping, knotting, or gluing. With flexible sleeve 314 lying axially within slot 312, the end of tag body 310 opposite slot 312 is inserted into hollow tip 154 of needle 152, and a length of flexible sleeve 314 with suture 150 fitted therein remains outside needle 152, as shown in FIG. 3C. T-tag device 300 is allowed to pass entirely into needle 152, while flexible sleeve 314 forms a protective barrier between suture 150 and the sharp inner edge 156 of needle 152. With T-tag device 300 loaded within needle 152, the user pushes needle 152 through first tissue 162 and then through second tissue 164. After needle 152 passes through second tissue 164, the user pushes a stylet (not shown) against the proximal end of T-tag device 300, which forces T-tag device 300 to exit needle 152. The user then withdraws needle 152 from first tissue 162 and second tissue 164 and, subsequently, applies traction upon suture 150. The pulling action upon suture 150 causes tag body 310 to pivot upon flexible sleeve 314 at the inner edge of slot 312, as flexible sleeve 314 forms a 90-degree angle (or nearly so) with slot 312 and, thus, tag body 310 aligns itself against second tissue 164, as shown in FIG. 3D. The user then locks and cuts the opposite end of flexible sleeve 314 with suture 150 fitted therein (locking and cutting mechanisms not shown).

Figure 4A:
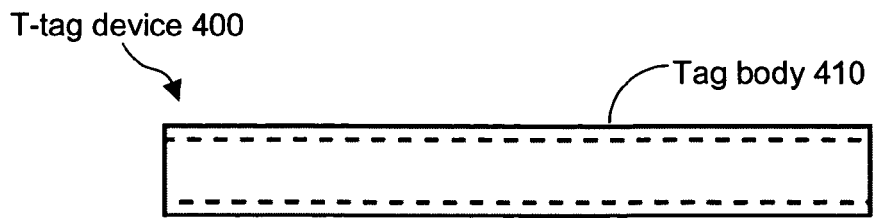
FIG. 4A illustrates a side view of a suture T-tag device in accordance with a fourth embodiment of the invention.
Figure 4B:
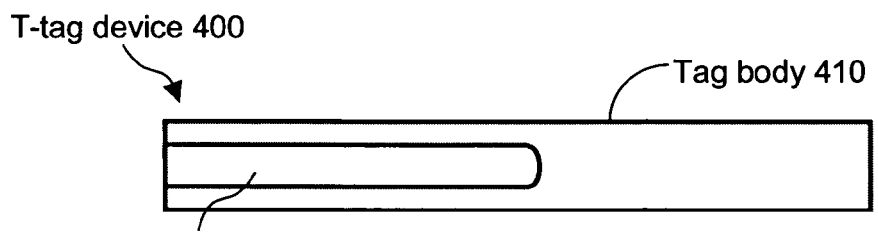
FIG. 4B illustrates a bottom view of the suture T-tag device of the fourth embodiment of the invention.

FIGS. 4A and 4B illustrate a side and bottom view, respectively, of a T-tag device 400 in accordance with a fourth embodiment of the invention. T-tag device 400 includes a cylindrical tag body 410. The outside diameter of tag body 410 is small enough to fit within the hollow tip of a standard EUS needle, which typically has an inside diameter of about 0.034 inches. The inside diameter of tag body 410 is sized to accommodate a preformed sleeve 414 (see FIG. 4C) that has suture 150 fitted therein. The outside diameter of preformed sleeve 414 typically ranges from 0.010 to 0.020 inches. T-tag device 400 further includes a slot 412 within the wall of tag body 410. Slot 412 runs from one end of tag body 410 to approximately midway of tag body 410 and is suitably wide enough to accommodate preformed sleeve 414 passing therethrough. T-tag device 400 is formed of, for example, molded plastic or stainless steel. Preformed sleeve 414 is formed of molded polymer material, such as a molded Polyimide tube. Preformed sleeve 414 is preformed at approximately a 90-degree angle at the region where preformed sleeve 414 emerges from slot 412 when deployed (described in detail in FIG. 4D).

Figure 4C:
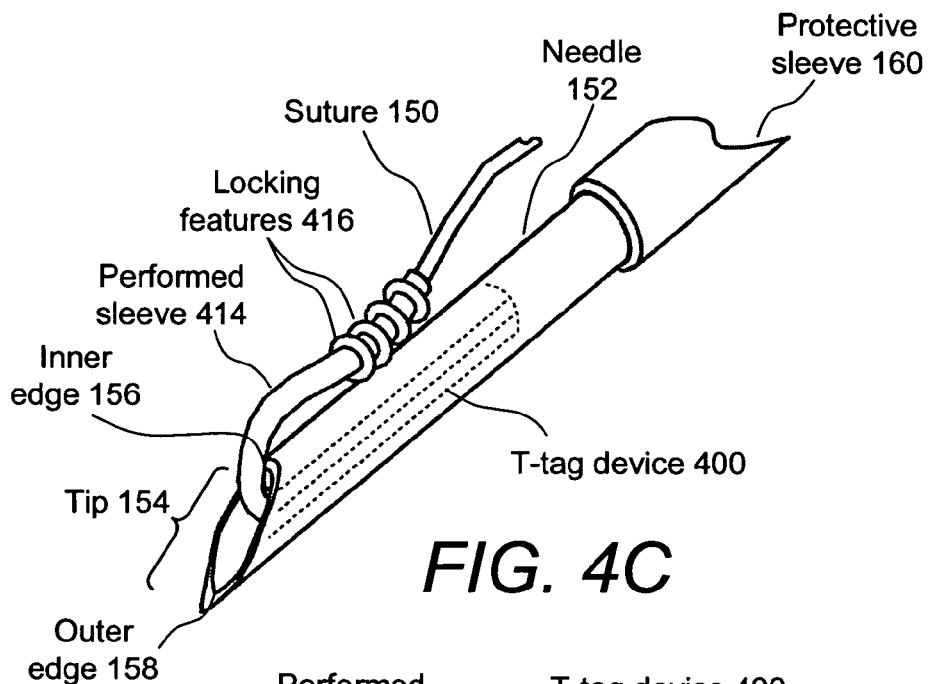
FIG. 4C illustrates a perspective view of the suture T-tag device of the fourth embodiment of the invention being deployed with a standard needle.

FIG. 4C illustrates a perspective view of T-tag device 400 of the fourth embodiment of the invention being deployed with a standard needle, such as a Wilson-Cook EUS needle. More specifically, FIG. 4C shows T-tag device 400 with preformed sleeve 414, within which suture 150 fitted, installed therein and inserted into the hollow tip of standard needle 152, which is slidable within protective sleeve 160. The sharp tip 154 of needle 152 is angled and, thus, its opening has an elliptical shape with sharp edges, i.e., inner edge 156 and outer edge 158, as described in reference to FIG. 1C. Preformed sleeve 414 provides a protective barrier between suture 150 and the sharp inner edge 156 of needle 152. Also shown in FIG. 4C, optionally, are a plurality of locking features 416 that are arranged along the proximal end of preformed sleeve 414. See Table 4 for example dimensions of T-tag device 400.

TABLE 4

Example dimensions of T-tag device 400

| | Example Dimension |
|---|---|
| Tag body 410 length | 0.25 inches |
| Tag body 410 outside diameter | 0.03 inches |
| Tag body 410 inside diameter | 0.02 inches |
| Slot 412 length | 0.125 inches |
| Slot 412 width | 0.02 inches |
| Preformed sleeve 414 length | 0.50 inches |
| Preformed sleeve 414 outside diameter | 0.015 inches |
| Preformed sleeve 414 inside diameter | 0.010 inches |
| Preformed sleeve 414 preformed region length | 0.03 inches |

Figure 4D:
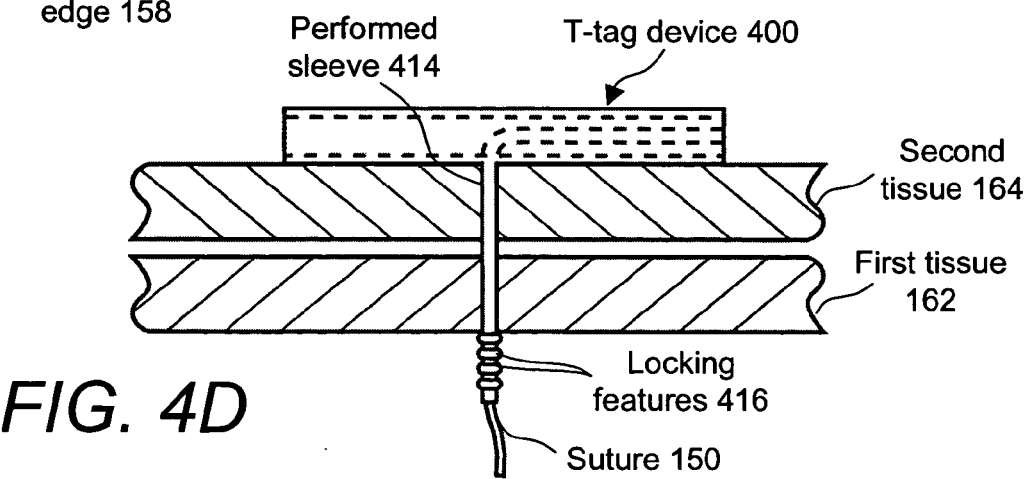
FIG. 4D illustrates a side view of the suture T-tag device of the fourth embodiment of the invention in use after being deployed.

The operation of T-tag device 400 is described in reference to FIGS. 4A, 4B, 4C, and FIG. 4D, which illustrates a side view of T-tag device 400 of the fourth embodiment of the invention in use after being deployed. An end of preformed sleeve 414 with suture 150 fitted therein is inserted through slot 412 and secured into the end of tag body 410 opposite slot 412. Methods of securing preformed sleeve 414 within tag body 410 include swaging, crimping, knotting, or gluing. With the preformed region of preformed sleeve 414 temporarily flattened, it lies axially within slot 412; the end of tag body 410 opposite slot 412 is inserted into hollow tip 154 of needle 152, and a length of preformed sleeve 414 with suture 150 fitted therein remains outside needle 152, as shown in FIG. 4C. T-tag device 400 is allowed to pass entirely into needle 152, while preformed sleeve 414 forms a protective barrier between suture 150 and the sharp inner edge 156 of needle 152. With T-tag device 400 loaded within needle 152, the user pushes needle 152 through first tissue 162 and then through second tissue 164. After needle 152 passes through second tissue 164, the user pushes a stylet (not shown) against the proximal end of T-tag device 400, which forces T-tag device 400 to exit needle 152. The user then withdraws needle 152 from first tissue 162 and second tissue 164 and, subsequently, applies traction upon suture 150. The pulling action upon suture 150, in combination with the preformed region of preformed sleeve 414's naturally seeking to restore its shape to 90 degrees, causes tag body 410 to pivot upon preformed sleeve 414 at the inner edge of slot 412, as preformed sleeve 414 forms a 90-degree angle (or nearly so) with slot 412 and, thus, tag body 410 aligns itself against second tissue 164, as shown in FIG. 4D. By using locking features 416 with an associated locking device, the user then locks and cuts the opposite end of preformed sleeve 414 with suture 150 fitted therein (locking and cutting mechanisms not shown).

Figure 5A:
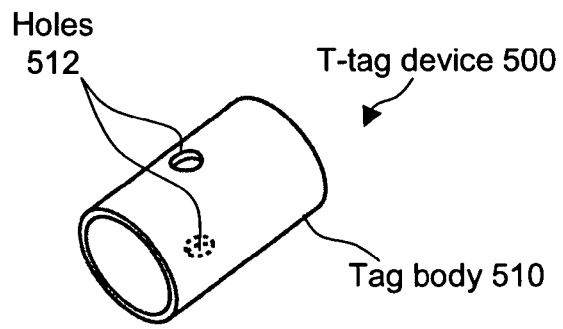
FIG. 5A illustrates a perspective view of a suture T-tag device in accordance with a fifth embodiment of the invention.

FIG. 5A illustrates a perspective view of a T-tag device 500 in accordance with a fifth embodiment of the invention. T-tag device 500 includes a cylindrical tag body 510. T-tag device 500 further includes two or more holes 512 spaced apart within the wall of tag body 510. The diameter of holes 512 is suitably large enough to accommodate suture 150 passing therethrough. T-tag device 500 is formed of, for example, molded plastic or stainless steel.

Figure 5B:
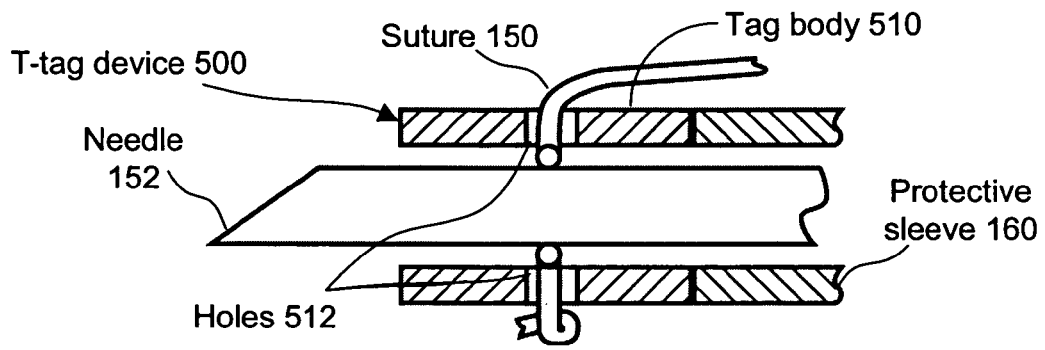
FIG. 5B illustrates a side view of the suture T-tag device of the fifth embodiment of the invention in combination with a standard needle.

FIG. 5B illustrates a side view of T-tag device 500 in accordance with a fifth embodiment of the invention in combination with a standard needle, such as a Wilson-Cook EUS needle. More specifically, FIG. 5B shows T-tag device 500 with suture 150 installed therein and disposed around the distal end of needle 152, which is slidable within protective sleeve 160. Suture 150 is secured to tag body 510 by the user's having threaded suture 150 in and out of holes 512 in an alternating fashion and then having knotted or glued suture 150 at one or more holes 512. Consequently, in order to provide a light press fit, the inside diameter of tag body 510 is slightly smaller than the total dimension of the outside diameter of needle 152 plus two times the thickness of suture 150. The outside diameter of tag body 510 is preferably equal to or less than the outside diameter of protective sleeve 160. Optionally, the edges of tag body 510 are tapered, in order to assist passage through body tissue. See Table 5 for example dimensions of T-tag device 500.

TABLE 5

Example dimensions of T-tag device 500

| | Example Dimension |
|---|---|
| Tag body 510 length | 0.25 inches |
| Tag body 510 outside diameter | 0.053 inches |
| Tag body 510 inside diameter | 0.043 inches |
| Holes 512 diameter | 0.012 inches |

Figure 5C:
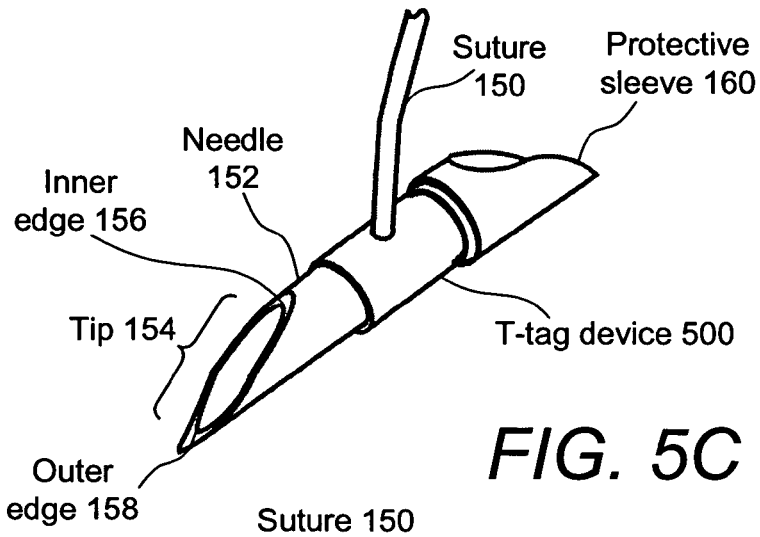
FIG. 5C illustrates a perspective view of the suture T-tag device of the fifth embodiment of the invention being deployed with a standard needle.

FIG. 5C illustrates a perspective view of T-tag device 500 of the fifth embodiment of the invention being deployed with a needle 152 and a length of suture 150 emerging from one of holes 512.

Figure 5D:
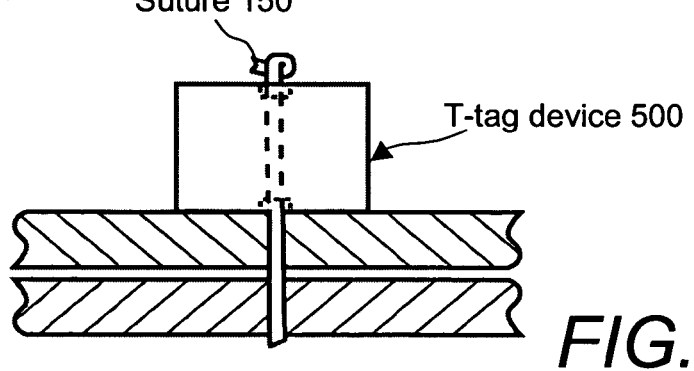
FIG. 5D illustrates a side view of the suture T-tag device of the fifth embodiment of the invention in use after being deployed.

The operation of T-tag device 500 is described in reference to FIGS. 5A, 5B, 5C, and FIG. 5D, which illustrates a side view of T-tag device 500 of the fifth embodiment of the invention in use after being deployed. An end of suture 150 is threaded in and out of holes 512 in an alternating fashion and then knotted or glued at one or more holes 512 of tag body 510. With suture 150 threaded therethrough, tip 154 of needle 152 is inserted into one end of tag body 510, and a length of suture 150 remains outside needle 152, as shown in FIG. 5C. Because suture 150 within T-tag device 500 is not in physical contact with the sharp inner edge 156 of needle 152, there is no danger of it's being cut. With T-tag device 500 loaded upon needle 152, the user pushes needle 152 and a portion of protective sleeve 160 through first tissue 162 and then through second tissue 164. After needle 152 passes through second tissue 164, the user retracts needle 152 within protective sleeve 160, which forces the end of protective sleeve 160 against tag body 510 and off needle 152. The user then withdraws protective sleeve 160 with needle 152 retracted therein from first tissue 162 and second tissue 164 and, subsequently, applies traction upon suture 150. The pulling action upon suture 150 causes tag body 510 to pivot upon suture 150 at one of holes 512 and form a 90-degree angle (or nearly so); thus, tag body 510 aligns itself against second tissue 164, as shown in FIG. 5D. The user then locks and cuts the opposite end of suture 150 (locking and cutting mechanisms not shown).

FIGS. 6A and 6B illustrate a side and bottom view, respectively, of a T-tag device 600 in accordance with a sixth embodiment of the invention. T-tag device 600 includes a cylindrical tag body 610. The outside diameter of tag body 610 is small enough to fit within the hollow tip of a standard EUS needle, which typically has an inside diameter of about 0.015 inches. The inside diameter of tag body 610 is sized to accommodate a metal suture 614 (see FIG. 6C), which is formed of a nontoxic metal, such as stainless steel or a nickel-titanium alloy, commercially known as Nitinol, a shape memory alloy, which has an outside diameter that typically ranges from 0.004 to 0.010 inches. T-tag device 600 further includes a slot 612 within the wall of tag body 610. Slot 612 runs from one end of tag body 610 to approximately midway of tag body 610 and is suitably wide enough to accommodate metal suture 614 passing therethrough. T-tag device 600 is formed of, for example, molded plastic or stainless steel.

FIG. 6C illustrates a perspective view of T-tag device 600 of the sixth embodiment of the invention being deployed with a standard needle, such as a Wilson-Cook EUS needle. More specifically, FIG. 6C shows T-tag device 600 with metal suture 614 installed therein and inserted into the hollow tip of standard needle 152, which is slidable within protective sleeve 160. The sharp tip 154 of needle 152 is angled and, thus, its opening has an elliptical shape with sharp edges, i.e., inner edge 156 and outer edge 158, as described in reference to FIG. 1C. Metal suture 614 is a material, suitably hard enough so that it is not cut against the sharp inner edge 156 of needle 152. In the case of metal suture 614's being formed of Nitinol, metal suture 614 has "memory" properties and high elasticity properties that allow it to be preformed at approximately a 90-degree angle at the region where metal suture 614 emerges from slot 612 when deployed (described in detail in FIG. 6D). See Table 6 for example dimensions of T-tag device 600.

TABLE 6

Example dimensions of T-tag device 600

| | Example Dimension |
|---|---|
| Tag body 610 length | 0.40 inches |
| Tag body 610 outside diameter | 0.034 inches |
| Tag body 610 inside diameter | 0.018 inches |
| Slot 612 length | 0.20 inches |
| Slot 612 width | 0.020 inches |
| Metal suture 614 outside diameter | 0.009 inches |
| Metal suture 614 length | 0.20 inches |

Furthermore, FIG. 6C shows a coupling/splice 616, which provides an interface for joining a length of metal suture 614 to another suture material, such as the typical polymer material of suture 150. Due to the difficulty in cutting metal suture 614, coupling/splice 616 provides a region that allows the physician to either release the polymer suture 150 (i.e., a coupling feature) or cut the polymer suture 150 (i.e., a splice feature).

The operation of T-tag device 600 is described in reference to FIGS. 6A, 6B, 6C, and FIG. 6D, which illustrates a side view of T-tag device 600 of the sixth embodiment of the invention in use after being deployed. An end of metal suture 614 is inserted through slot 612 and secured into the end of tag body 610 opposite slot 612. Methods of securing metal suture 614 within tag body 610 include swaging, crimping, knotting, or gluing. With metal suture 614 lying axially within slot 612, the end of tag body 610 opposite slot 612 is inserted into hollow tip 154 of needle 152, and a length of metal suture 614 remains outside needle 152, as shown in FIG. 6C. T-tag device 600 is allowed to pass entirely into needle 152 and, because of its hard material properties, metal suture 614 is unable to be cut by the sharp inner edge 156 of needle 152. With T-tag device 600 loaded within needle 152, the user pushes needle 152 through first tissue 162 and then through second tissue 164. After needle 152 passes through second tissue 164, the user pushes a stylet (not shown) against the proximal end of T-tag device 600, which forces T-tag device 600 to exit needle 152. The user then withdraws needle 152 from first tissue 162 and second tissue 164 and, subsequently, applies traction upon metal suture 614. The pulling action upon metal suture 614 in combination, optionally, with the preformed region of metal suture 614's naturally seeking to restore its shape to 90 degrees, causes tag body 610 to pivot upon metal suture 614 at the inner edge of slot 612, as metal suture 614 forms a 90-degree angle (or nearly so) with slot 612 and, thus, tag body 610 aligns itself against second tissue 164, as shown in FIG. 6D. The user then locks metal suture 614 (locking mechanism not shown) and either releases the polymer suture 150 (i.e., a coupling feature) or cuts the polymer suture 150 (i.e., a splice feature) at coupling/splice 616.

Figure 7:
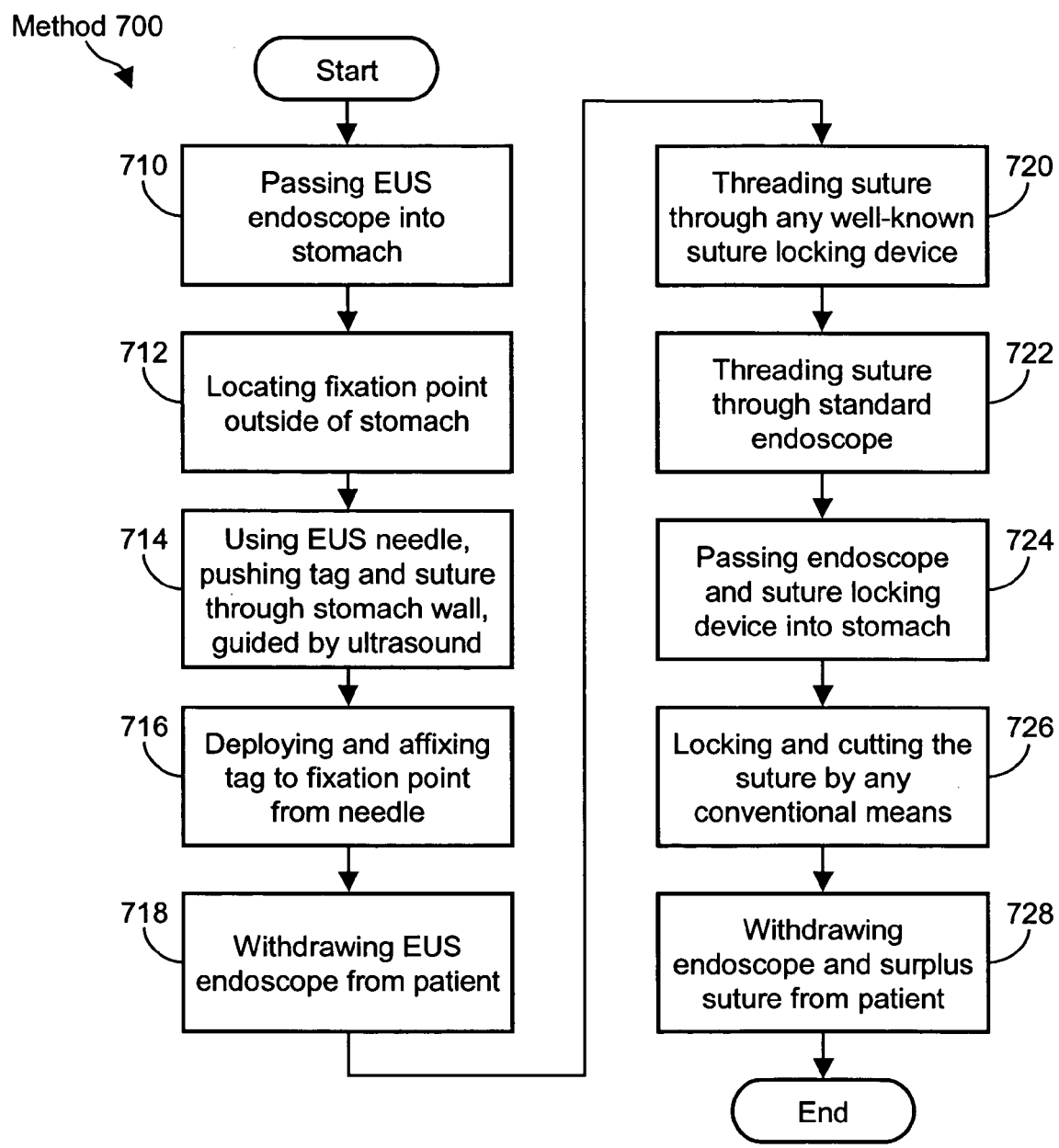
FIG. 7 illustrates a flow diagram of an example method of using the T-tag devices in accordance with embodiments one through six of the present invention.

FIG. 7 illustrates a flow diagram of an example method 700 of using the T-tag devices in accordance with embodiments one through six of the present invention. More specifically, method 700 provides an example of a posterior gastropexy procedure that uses the T-tag devices of the present invention. The use of the T-tag devices of the present invention is not limited to a posterior gastropexy procedure; the T-tag devices of the present invention may be used in any of various, similar medical procedures.

At step 710, a physician passes an EUS endoscope through a patient's mouth and esophagus and into the stomach. Example EUS endoscopes include endoscope model GF-UC160P-AT8, manufactured by Olympus Europe (Hamburg, Germany) and endoscope model EG-3630U, manufactured by Pentax Medical Company (Orangeburg, N.Y.). The working channel of the EUS endoscope is preloaded with a standard EUS needle, such as is manufactured by Wilson-Cook (Winston-Salem, N.C.), that serves as a carrier for a tag and thread, such as T-tag devices 100, 200, 300, 400, or 500, with suture 150, or T-tag device 600 with metal suture 614. The sutures may run either through the needle or outside the needle, but still inside the working channel of the EUS endoscope; alternatively, the sutures can run along the outside of the EUS endoscope.

At step 712, under the guidance of the EUS endoscope, the physician locates and identifies structures outside of the stomach wall and selects a fixation point, such as the median arcuate ligament.

At step 714, under the guidance of the EUS endoscope, the physician pushes the EUS needle (i.e., needle 152), which is carrying T-tag device 100, 200, 300, 400, or 500 with suture 150 or T-tag device 600 with metal suture 614, through the stomach wall, which is represented by first tissue 162 in FIGS. 1D, 2D, 3D, 4D, 5D, and 6D.

At step 716, under the guidance of the EUS endoscope, the physician deploys and affixes T-tag device 100, 200, 300, 400, or 500, with suture 150 attached thereto, or T-tag device 600 with metal suture 614 attached thereto, to the fixation point, such as to the MAL, which is represented by second tissue 164 in FIGS. 1D, 2D, 3D, 4D, 5D, and 6D. The deployment of T-tag device 100 is as described in reference to FIGS. 1A, 1B, 1C, and 1D. The deployment of T-tag device 200 is as described in reference to FIGS. 2A, 2B, 2C, and 2D. The deployment of T-tag device 300 is as described in reference to FIGS. 3A, 3B, 3C, and 3D. The deployment of T-tag device 400 is as described in reference to FIGS. 4A, 4B, 4C, and 4D. The deployment of T-tag device 500 is as described in reference to FIGS. 5A, 5B, 5C, and 5D. The deployment of T-tag device 600 is as described in reference to FIGS. 6A, 6B, 6C, and 6D.

At step 718, the physician withdraws the EUS endoscope and associated instrumentation from the patient, but leaves a length of suture 150 or metal suture 614 still threaded through the patient's gastroesophageal tract and anchored to second tissue 142 (e.g., MAL). The length of suture 150 or metal suture 614 extends out of the patient's mouth and is accessible to the physician.

At step 720, the physician threads the length of suture 150 or metal suture 614 that is extending out of the patient's mouth through any well-known suture locking device.

At step 722, the physician threads the length of suture 150 or metal suture 614 that is extending out of the well-known suture locking device through the working channel of a standard endoscope that has a standard vision system (i.e., not an EUS endoscope).

At step 724, while holding tension on suture 150 or metal suture 614, the physician passes a standard endoscope that has a standard vision system (i.e., not an EUS endoscope) and the suture locking device through the patient's mouth and esophagus and into the stomach. The suture locking device is sliding freely along suture 150 or metal suture 614.

At step 726, having determined that the desired geometry change between the stomach and the MAL (represented by first tissue 162 and second tissue 164) is achieved and while continuing to hold tension on suture 150 or metal suture 614, the physician locks and cuts suture 150 or metal suture 614 by any conventional means.

At step 728, the physician withdraws the endoscope and surplus material of suture 150 or metal suture 614 from the patient. Method 700 ends.

In an alternative embodiment, method 700 uses a single EUS endoscope device that also has a standard vision system. As a result, only one endoscope device is needed throughout the entirety of method 700. In this case, the EUS endoscope device with a standard vision system is passed into the patient at step 710. It need not be withdrawn at step 718, and a second standard endoscope need not be passed into the patient at step 724.

While the present invention has been illustrated by description of various embodiments, it is not the intention of the applicants to restrict or limit the spirit and scope of the appended claims to such detail. Numerous other variations, changes, and substitutions will occur to those skilled in the art without departing from the scope of the invention. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed is:

1. A medical device for anchoring suture comprising:
a surgical needle comprising a tip with a sharp edge, a lumen, and an outer surface;
a tag body positioned in the lumen of the surgical needle, the tag body having a length;
a suture attached to a portion of said tag body, the suture comprising an elongate length greater than the tag body length, the elongate length of suture extending outside of the tag body and distally from the tip of the surgical needle while the tag body is positioned in the lumen of the surgical needle; and
a protective sleeve positioned around the outer surface of the surgical needle, the protective sleeve being dimensioned and adapted to pass through the working channel of a flexible endoscope, the protective sleeve being axially slideable relative the surgical needle between a first position over the tip and a second position where the tip is exposed;

wherein in the first position the elongate length of suture extends distally from the tip of the surgical needle and distally from the protective sleeve.

2. The medical device of claim 1, further comprising a flexible sleeve covering a portion of said suture distal from the tag body and coincident with the sharp edge of the surgical needle tip.

3. The medical device of claim 2 wherein said flexible sleeve comprises a polyamide tube.

4. The medical device of claim 1 wherein said tag body comprises a cylindrical body and a slot in said cylindrical body extending along a long axis of said cylindrical body.

5. The medical device of claim 1 wherein said suture is constructed of a metal fiber.

6. The medical device of claim 1 wherein said needle is an endoscopic ultrasound needle.

7. The medical device of claim 1 wherein said tag body has an outside diameter of no more than about 0.030 inches.

8. A medical device for anchoring suture comprising:
a surgical needle comprising a tip with a sharp edge, a lumen, and an outer surface;
a tag body positioned in the lumen of the surgical needle, the tag body having a length;
a suture attached to a portion of said tag body, the suture comprising an elongate length greater than the tag body length, the elongate length of suture extending outside of the tag body and distally from the tip of the surgical needle while the tag body is positioned in the lumen of the surgical needle; and
a protective sleeve positioned around the outer surface of the surgical needle, the protective sleeve being dimensioned and adapted to pass through the working channel of a flexible endoscope, the protective sleeve and surgical needle being slideable relative one another between a first position where the protective sleeve extends over the tip and a second position where the tip is exposed; and wherein in the first position the protective sleeve protects the sharp edge of the surgical needle tip.

9. The medical device of claim 8, further comprising a flexible sleeve covering a portion of said suture distal from the tag body and coincident with the sharp edge of the surgical needle tip.

10. The medical device of claim 9 wherein said flexible sleeve comprises a polyamide tube.

11. The medical device of claim 8 wherein said tag body comprises a cylindrical body and a slot in said cylindrical body extending along a long axis of said cylindrical body.

12. The medical device of claim 8 wherein said suture is constructed of a metal fiber.

13. The medical device of claim 8 wherein said needle is an endoscopic ultrasound needle.

14. The medical device of claim 8 wherein said tag body has an outside diameter of no more than about 0.030 inches.

15. The medical device of claim 8 wherein in the first position the elongate length of suture extends distally from the tip of the surgical needle and distally from the protective sleeve.

16. A medical device for anchoring suture comprising:
a surgical needle comprising a tip with a sharp edge, a lumen, and an outer surface;
a tag body positioned in the lumen of the surgical needle, the tag body having a slotted end with a lateral slot and an unslotted end;
a suture attached to a portion of said tag body, the suture comprising an elongate length extending out from the slotted end of the tag body and extending distally from the tip of the surgical needle while the tag body is positioned in the lumen; and
a protective sleeve positioned around the outer surface of the surgical needle, the protective sleeve being dimensioned and adapted to pass through the working channel of a flexible endoscope, the protective sleeve and surgical needle being slideable relative one another between a first position where the protective sleeve extends over the tip and a second position where the tip is exposed.

* * * * *